United States Patent [19]

Ahjopalo

[11] 4,412,917
[45] Nov. 1, 1983

[54] WEIGHT CONTROLLED AND HYDROSTATIC PRESSURE ADJUSTABLE PERITONEAL DIALYSIS APPARATUS

[75] Inventor: Hannu T. Ahjopalo, Helsinki, Finland

[73] Assignee: Instrumentarium oy, Helsinki, Finland

[21] Appl. No.: 266,285

[22] Filed: May 22, 1981

[30] Foreign Application Priority Data

May 28, 1981 [FI] Finland .................................. 801718

[51] Int. Cl.³ .......................................... B01D 31/00
[52] U.S. Cl. .................................... 210/104; 210/110; 210/137; 210/257.2; 210/321.3; 604/29
[58] Field of Search ........... 128/213 A, 214 A, 214 B, 128/400, DIG. 3, DIG. 13; 210/86, 93, 103, 104, 110, 137, 321, 181, 257.2; 604/29

[56] References Cited

U.S. PATENT DOCUMENTS

| | | | |
|---|---|---|---|
| 3,730,183 | 5/1973 | Goldsmith et al. | 128/213 A |
| 3,783,866 | 1/1974 | Tirkkonen | 128/213 A |

FOREIGN PATENT DOCUMENTS

| | | | |
|---|---|---|---|
| 48674 | 6/1974 | Finland | 128/213 A |

*Primary Examiner*—David R. Sadowski
*Attorney, Agent, or Firm*—Andrus, Sceales, Starke & Sawall

[57] ABSTRACT

An apparatus for peritoneal dialysis including a first vessel to contain dialysis fluid and a second vessel to contain spent dialysis fluid. The first and second vessels are connected through a conduit means with the abdominal cavity of a patient, and a pump is located in the conduit means between the first vessel and the abdominal cavity to pump dialysis fluid into the cavity, while a flow control means, such as a valve, is located in the conduit means between the abdominal cavity and the second vessel to control the flow of dialysis fluid being removed from the patient. A branch conduit interconnects the conduit means at a location between the first vessel and the abdominal cavity and the branch conduit is provided with a third overflow vessel located at a higher level than the abdominal cavity. A weighing mechanism is provided for weighing all three vessels, and a control unit is responsive to the weight as determined by the weighing mechanism for controlling operation of the pump and the valve means to obtain the desired flow of dialysis fluid through the conduit means.

7 Claims, 5 Drawing Figures

WEIGHT CONTROLLED AND HYDROSTATIC PRESSURE ADJUSTABLE PERITONEAL DIALYSIS APPARATUS

BACKGROUND OF THE INVENTION

Peritoneal dialysis with various ways of performing it has established its position in the treatment of kidney patients. Its advantages over other dialysis methods include simplicity of the method itself and patient security. However, peritoneal dialysis is not as yet used as often as it could in view of its potential possibilities. A reason for this is the slowness and inefficiency of the present peritoneal dialyzers in view of e.g. hemodialysis, a single treatment taking unreasonably long time.

The object of the apparatus of this invention is to make it possible to perform peritoneal dialysis quickly, effectively and at the same time in completely controlled manner, whereby changes in a patient's fluid balance and disturbances in the flow of fluid can be taken into consideration. The apparatus as such must be applicable to conventional periodical peritoneal dialysis as well as to so-called continuous flow dialysis in which, by means of a double-catheter or two regular catheters, fluid is continuously maintained in motion in a patient's abdominal cavity.

On the above basis, the present invention relates to a peritoneal dialyzer, comprising a dialysis fluid vessel, a vessel for used fluid, a scales for weighing the vessels, a tubing system between the vessels and a patient, at least one pump for pumping the dialysis fluid into a patient, a valve (or a pump) for controlling the amount of dialysis fluid to be removed from a patient, and a control unit which is connected so as to be controlled by the scales and in turn controls the pump and the valve (or another pump).

Finnish Patent Publication No. 48674 discloses a peritoneal dialyzer in which, in order to determine the fluid balance, the dialysis fluid vessel and the used fluid vessel are weighed together. Dialysis fluid is passed from the vessel into a patient by means of static fluid pressure controlled by a valve which again is controlled by a scales. However, the static fluid pressure and resulting flow rate varies according to the degree of filling and size of the vessel. This could be eliminated by using a pump for such fluid supply but, on the other hand, the use of a pump leads to a substantial safety hazard unless the pressure of the fluid delivered into a patient is restricted one way or the other.

SUMMARY OF THE INVENTION

The object of the invention is to provide an improved peritoneal dialyzer which combines the advantages of free fluid flow with those of pumping while, at the same time, a patient's safety and versatile applications of the apparatus are secured.

For this object, the apparatus of the invention is characterized in that downstream of the pump the dialysis fluid supply tube is branched on one hand into a section leading to a patient and, on the other hand, into a section leading to an overflow and pressure equalizing vessel, which acts as a pressure control means for the dialysis fluid to be pumped, said overflow and pressure equalizing vessel being arranged to be weighed by the scales together with the dialysis fluid vessel and the used fluid vessel. Thus, the overflow and pressure equalizing vessel acts as a pressure control means and as an important safety factor to render the use of a pump possible. Another important feature is to weigh the overflow and pressure equalizing vessel together with the dialysis fluid vessel and the used fluid fluid vessel, this being the factor which provides for the control over a patient's fluid balance.

According to a preferred embodiment of the invention, the overflow and pressure equalizing vessel is provided with a limit switch connected to a control unit for transmitting a control signal as soon as said vessel contains a predetermined amount of fluid. By virtue of the limit switch, the size of an overflow and pressure equalizing vessel can be restricted and to make sure in all conditions that the pressure fed into a patient does not exceed a predetermined level.

According to another preferred embodiment of the invention, the scales unit is mounted on a cart for transporting the vessels to be weighed. This provides for handy transport of fluids and the vessels can be positioned on quite a low level which makes the apparatus substantially easier to operated as compared to the apparatus disclosed in the Finnish Patent Publication No. 48674.

The feed pressure limit value can be readily regulated by making the positional level of an overflow and pressure equalizing vessel adjustable.

DESCRIPTION OF THE DRAWINGS

The following is a more detailed description of the invention with reference made to the accompanying drawings, in which.

DESCRIPTION OF THE ILLUSTRATED EMBODIMENT

Figure 1:
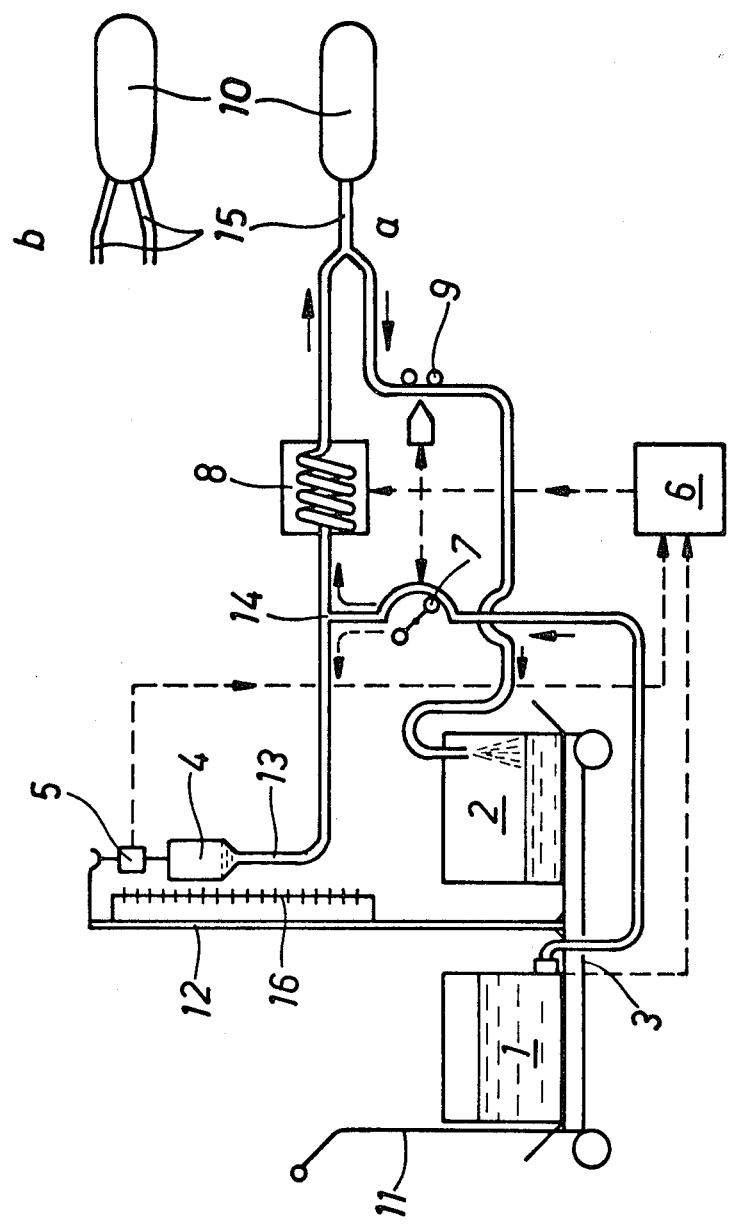
FIG. 1 is a schematic view of an apparatus of the invention.

As for the operation of the apparatus, the most significant components are presented in FIG. 1 A scales unit 3 is so disposed that the total weight of a fresh dialysis fluid containing vessel 1, an overflow vessel 4 and a used fluid vessel 2 can be measured. The operation is controlled by a central unit 6 which, in addition to the weighing data, receives a signal from a limit switch 5 indicating that the overflow vessel contains a predetrmined amount of fluid.

The central unit controls a dialysis fluid pump 7 and a discharge valve 9 (may also be a pump), as well as a fluid heater 8. The latter can also be operationally independent of the central unit and its alternative position can be between the pump and a T-joint 14.

Connection of a patient's abdominal cavity to the apparatus can be accomplished either through one catheter 15 (alternative a) or via two cathetesa/a double-catheter (alternative b).

In view of the operation of the apparatus, it is preferable to mount the scales unit with its fluid vessels on a cart 11 by means of which the fluids can be transported before and after the treatment.

Figure 2:
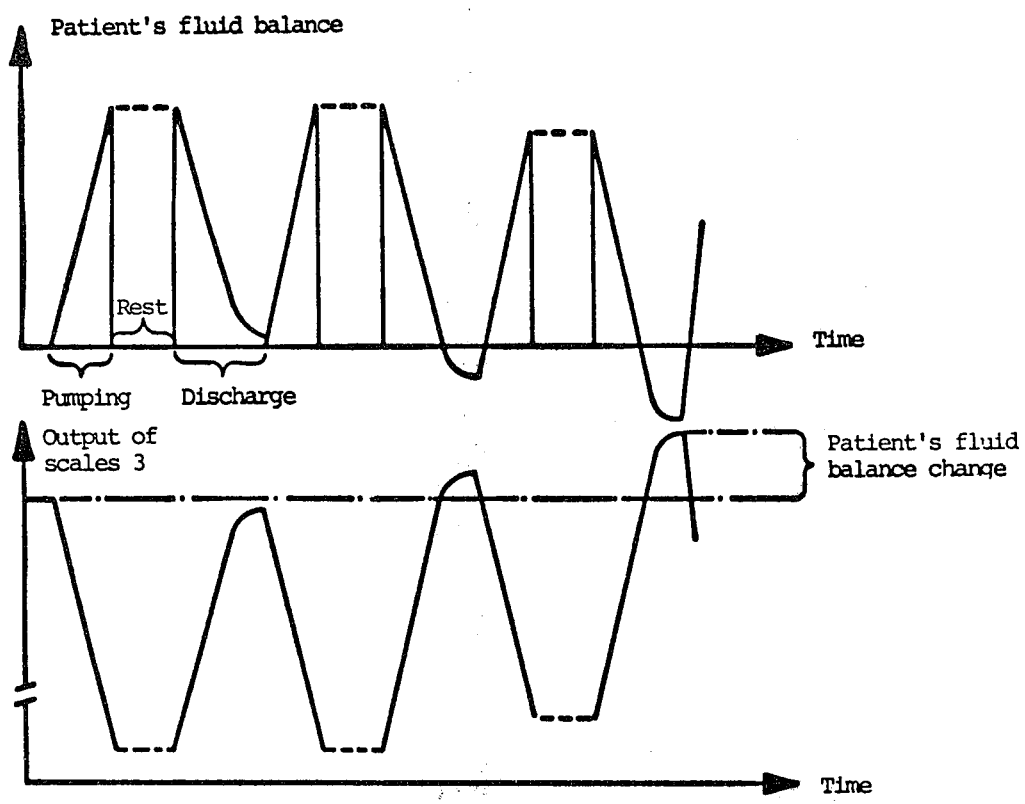
FIGS. 2 and 3 show the flow sheets of the apparatus in periodic operation.
Figure 3:
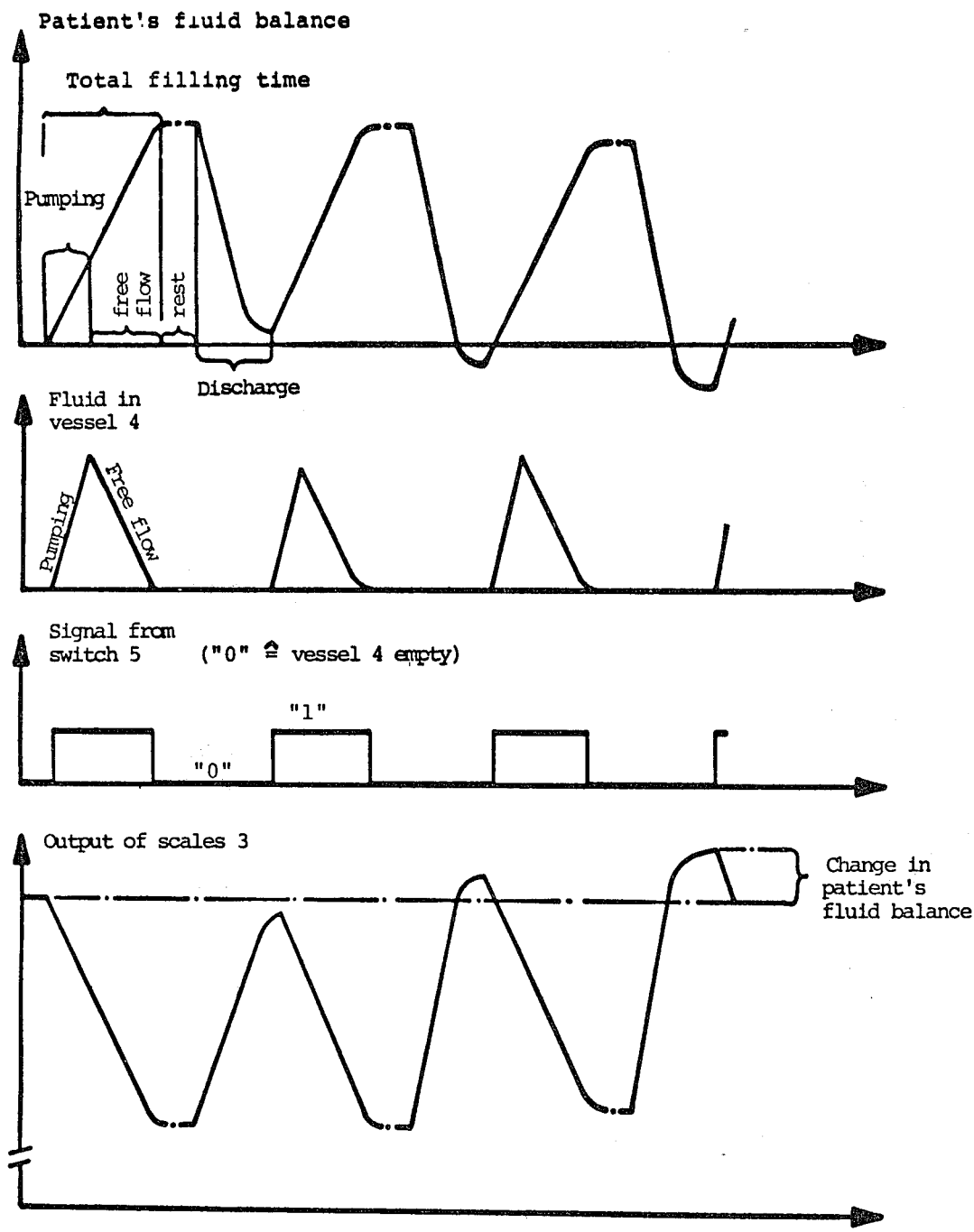

The apparatus is operated as follows. As pointed out above, the apparatus can be used for both periodic and continuous flow dialysis. The operation is principally the same in both cases. The periodic operation is illustrated in the diagrams of FIGS. 2 and 3.

The abdominal cavity of a patient is filled so that the pump 7 delivers a dose of dialysis fluid from vessel 1 through heater 8 into the abdominal cavity 10. The filling pressure and rate can be controlled, not only by the regulation of pumping rate, but also by adjusting the height of a rod 12, whereby the height of a liquid column in a line 13 and in the overflow vessel 4 as well as the resulting static fluid pressure in the three-way connection 14 are changed. The height of rod 12 is selected so that in its top position the liquid column does not reach the vessel 4 (provided that there is no block in the tube system or catheter), the fluid delivered by the pump thus passing immediately to the right of the joint 14 (into a patient).

When the vessel 4 is lowered, the liquid flow is branched at the joint, some of the fluid passing into a patient and some being collected in the vessel. Provided that said overflow vessel is disposed higher than the abdominal cavity of a patient, this fluid will also flow into the abdominal cavity by the action of gravity after the pumping operation.

The fluid dosage received by a patient can be controlled both by counting pump revolutions or pumping time (rough estimation) and by monitoring the total weight of vessels (1, 2, 4), whereby the weight reduction equals the amount of fluid received by a patient. It should be noted that rod 12, overflow vessel 4 and line 13 are mounted on the scales unit 3.

Discharge of the abdominal cavity is effected either immediately after the filling or after a determined rest period by opening a heretofore closed valve 9, the fluid thus flowing into a waste vessel 2. Following the discharge operation, a patient's fluid balance is determined on the basis of the weighing output of scales unit 3, whereby the increase in total weight equals the extra amount of fluid, i.e. ultrafiltrate received from a patient.

The above operation cycles are repeated until a desired amount of fluid is used or the change in fluid balance reported by the scales unit is of the desired order. The treatment can be programmed to terminate on the basis of either one of the above criteria.

Figure 4:
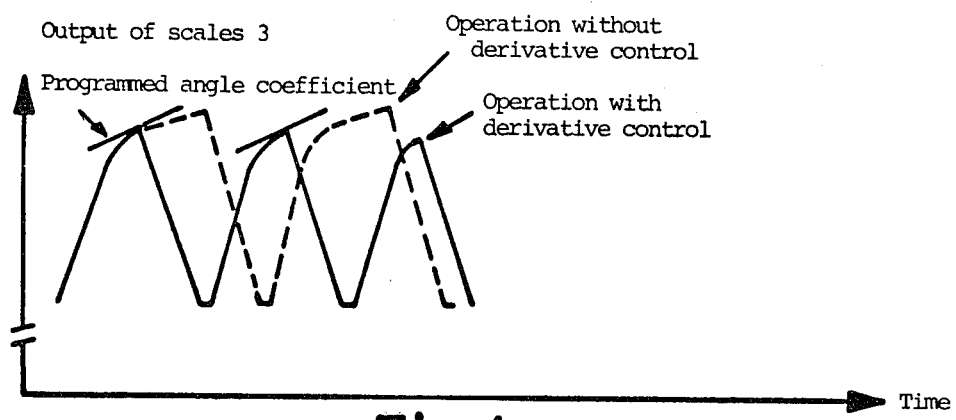
FIG. 4 illustrates the way the present apparatus makes it possible to optimize the dialysis on the basis of a change in the outflow rate.

The necessary treatment time can be shortened and dialysis intensified by programming the derivate of scales signal so as to determine the closing moment of valve 9 and the starting moment of pump 7 (FIG. 4).

This is based on the fact that flowing out of the abdominal cavity slows down considerably when 70 to 80% of the fluid dosage has come out. If the discharge is interrupted at this stage, the next filling can be initiated earlier and the inactive dialysis time reduced.

For the control of filling pressure it is possible to mount on the side of stand 12 a pressure gauge (vertical) 16 (mm H2O can be calibrated e.g. to kPa), the zero point of said gauge being set on the level of a patient's abdominal cavity.

In the continuous flow method, a patient is connected to the apparatus by two separate catheters or by a double-catheter in which the fluid supply into and removal from the abdominal cavity are effected through different parts of the catheter.

Figure 5:
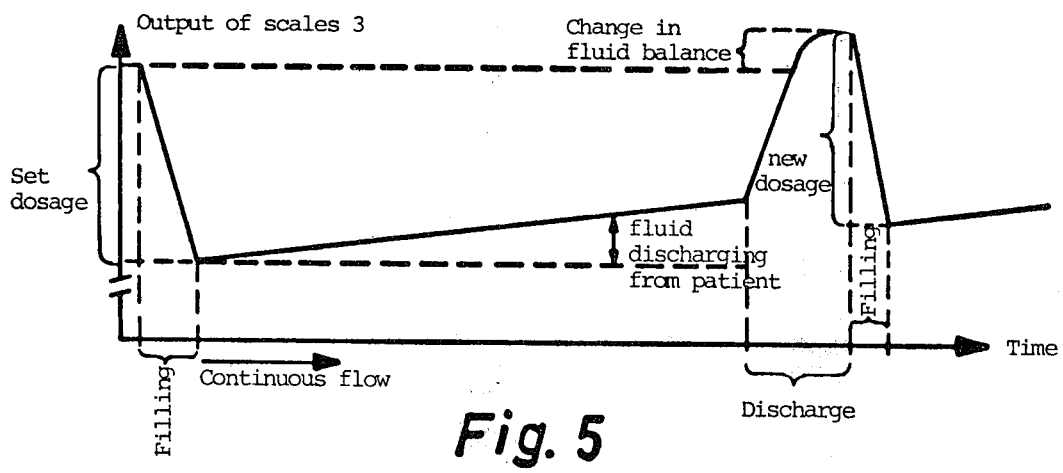
FIG. 5 illustrates the programmed steady removal of ultrafiltrate from a patient in continuous flow dialysis as achieved by the apparatus of the invention.

The operation starts the same way as discussed above. When a patient has received a desired dosage of fluid, pump 7 is not, however, stopped. By opening valve 9, the total amount of fluid in a patient is kept constant or the amount of fluid is increased or decreased according to a selected program. In practice, an important aspect is steady reduction of the amount of fluid in a patient ideally in such a manner that the fluid excess withdrawn from the patient corresponds to ultrafiltrate. Thus, the continuous amount of fluid in a patient's abdominal cavity stays constant (FIG. 5) and, thus, by re-measuring the total weight of fluid vessels the operation of valve 9 and pump 7 is controlled. The abdominal cavity can be emptied at fixed intervals, if desired, whereby changes in a patient's fluid balance can be accurately recorded on the basis of weight increase displayed by the scales unit 3. Thereafter, the abdominal cavity is re-filled and dialysis continued.

The operation of the apparatus has been discussed above considering that the dialysis fluid to be used is in vessel 1 from the beginning. However, this is not necessary but, e.g. if use is made of a separate apparatus producing dialysis fluid, vessel 1 can be periodically filled. The flow into/out of a patient must be interrupted for filling and the scales unit 3 must be zeroed. This can be done automatically under the control of a control unit 6 and, after the filling, operation is continued.

I claim:

1. An apparatus for peritoneal dialysis, comprising a first vessel to contain a dialysis fluid; a second vessel to contain spent dialysis fluid; conduit means for interconnecting said first and second vessels with the abdominal cavity of a patient; pumping means in said conduit means for pumping the dialysis fluid directly into the abdominal cavity; flow control means in said conduit means for controlling the amount of dialysis fluid removed from said abdominal cavity; a branch conduit interconnected with said conduit means at a location between said pumping means and said abdominal cavity and having a hydrostatic pressure equalizing section disposed at a higher level than said abdominal cavity, said pumping means and conduit means providing fluid flow into the abdominal cavity simultaneously with pumping against hydrostatic liquid pressure in said pressure equalizing section; weighing means for measuring the weight of said first vessel, said second vessel, and said equalizing section; and control means operably connected to said pumping means and to said flow control means and responsive to the weight as determined by said weighing means for controlling the operation of said pumping means and said flow control means to obtain the desired flow of fluid through said conduit means.

2. The apparatus of claim 1, wherein said pump means is disposed in said conduit means between said first vessel and said branch conduit.

3. The apparatus of claim 1, and including heating means for heating said dialysis fluid, said heating means being located in said conduit means between said first vessel and said abdominal cavity for heating the fluid as it flows through said conduit means.

4. The apparatus of claim 1, and including pressure regulating means for regulating the pressure of the dialysis fluid introduced into said abdominal cavity.

5. The apparatus of claim 4, wherein said pressure regulating means includes means for adjusting the vertical position of said pressure equalizing section relative to said abdominal cavity.

6. The apparatus of claim 1, wherein said pressure equalizing section comprises a third vessel.

7. The apparatus of claim 6, and including sensing means operably connected to said control means and responsive to a predetermined level of dialysis fluid in said third vessel for controlling operation of said pumping means.

* * * * *